US012797120B2

(12) United States Patent
Hao et al.

(10) Patent No.: US 12,797,120 B2
(45) Date of Patent: Nov. 17, 2026

(54) SURGICAL SMOKING KNIFE

(71) Applicant: Zhejiang Shuyou Instrument Equipment Co., Ltd., Huzhou (CN)

(72) Inventors: Tai Hao, Huzhou (CN); Ying Su, Huzhou (CN); Xianfeng Zhou, Huzhou (CN); Zuokai Yin, Huzhou (CN); Kongpei Lu, Huzhou (CN)

(73) Assignee: Zhejiang Shuyou Instrument Equipment Co., Ltd., Huzhou (CN)

(*) Notice: Subject to any disclaimer, the term of this patent is extended or adjusted under 35 U.S.C. 154(b) by 186 days.

(21) Appl. No.: 18/752,709

(22) Filed: Jun. 24, 2024

(65) Prior Publication Data

US 2024/0423696 A1 Dec. 26, 2024

Related U.S. Application Data

(63) Continuation of application No. PCT/CN2023/106964, filed on Jul. 12, 2023.

(30) Foreign Application Priority Data

Jun. 25, 2023 (CN) ........................ 202310751969.1

(51) Int. Cl.

| | |
|---|---|
| ***A61B 18/14*** | (2006.01) |
| ***A61B 90/30*** | (2016.01) |
| ***F21V 3/02*** | (2006.01) |
| ***F21V 17/02*** | (2006.01) |
| *A61B 18/00* | (2006.01) |

(Continued)

(52) U.S. Cl.

CPC .......... *A61B 18/1402* (2013.01); *A61B 90/30* (2016.02); *F21V 3/02* (2013.01); *F21V 17/02* (2013.01); *A61B 2018/00601* (2013.01); *A61B 2018/1412* (2013.01);

(Continued)

(58) Field of Classification Search

CPC ...... A61B 18/1402; A61B 2018/00595; A61B 2018/00601; A61B 2018/1412; A61B 2090/309; A61B 2218/008; A61B 90/30; F21W 2131/20

See application file for complete search history.

(56) References Cited

U.S. PATENT DOCUMENTS 5,413,575 A * 5/1995 Haenggi ............ A61B 18/1402 606/45
9,987,074 B2 * 6/2018 Ineson ............... A61B 18/1402

(Continued)

FOREIGN PATENT DOCUMENTS

| | | | |
|---|---|---|---|
| CN | 110934637 | A | 3/2020 |
| CN | 213098272 | U | 5/2021 |
| CN | 217772497 | U | 11/2022 |

*Primary Examiner* — Michael F Peffley

(74) *Attorney, Agent, or Firm* — JEEN IP LAW, LLC

(57) ABSTRACT

The invention discloses a surgical smoking knife, which includes: a casing with a slide inside; a smoking tube slidably connected to the slide, with one part located inside the casing and the other part located outside the casing; and an electrode knife disposed on the smoking knives. on the pipe; a control circuit board is arranged on the housing; a flexible transmission circuit slat penetrates into the inside of the smoking pipe through a slide, and its two ends are connected to the control circuit board and the electrode knife respectively. The beneficial effect of the present invention is that it can effectively reduce the friction resistance during telescopic adjustment.

7 Claims, 7 Drawing Sheets

(51) Int. Cl.
*F21W 131/20* (2006.01)
*F21Y 115/10* (2016.01)

(52) U.S. Cl.
CPC ... *A61B 2090/309* (2016.02); *A61B 2218/008* (2013.01); *F21W 2131/20* (2013.01); *F21Y 2115/10* (2016.08)

(56) References Cited

U.S. PATENT DOCUMENTS

| | | | | |
|---|---|---|---|---|
| 10,342,607 | B1 * | 7/2019 | Reaux | A61B 18/1206 |
| 2006/0264928 | A1 * | 11/2006 | Kornerup | A61B 18/1402 606/49 |
| 2011/0190768 | A1 * | 8/2011 | Shvetsov | A61B 90/30 606/48 |
| 2018/0078301 | A1 * | 3/2018 | Vayser | A61B 18/1402 |
| 2024/0074808 | A1 * | 3/2024 | Lu | A61B 18/14 |

* cited by examiner

SURGICAL SMOKING KNIFE

CROSS-REFERENCE TO RELATED APPLICATIONS

The application claims priority to Chinese patent application No. 202310751969.1, filed on Jun. 25, 2023, the entire contents of which are incorporated herein by reference.

TECHNICAL FIELD

The invention relates to a surgical smoking knife and belongs to the technical field of surgical equipment.

BACKGROUND

The surgical smoking knife in this implementation case belongs to the high-frequency electrosurgical knife, which is an electrosurgical medical device that replaces the mechanical scalpel for tissue cutting. High-frequency electrosurgery produces smoke and dust during the operation and is discharged through the smoking tube.

For example, the patent application with the prior art publication number CN108742833A discloses a smoking high-frequency scalpel, there are two double-sided PCB boards built into the cavity of the scalpel, the PCB board connects the electric shock knife and the LED light source through lines, since The delivery connection line or delivery connection plate configured on the PCB board has poor bend-ability and many contact parts, it is easy to generate large friction resistance when telescopically sliding the scalpel, making it more laborious for doctors to adjust the length of the scalpel, which is not conducive to surgical operation.

SUMMARY

The technical problem to be solved by the present invention is to provide a surgical smoking knife that can effectively reduce the friction resistance during telescopic adjustment.

The present invention is achieved through the following technical solutions.

A surgical smoking knife, including:

A shell with a slide inside;

The smoking pipe is slidably connected to the slide, with one part located inside the housing and the other part located outside the housing;

An electrode knife is arranged on the smoking pipe;

A control circuit board is provided on the housing;

The flexible conveying circuit slat penetrates into the inside of the smoking pipe through the slide, and its two ends are respectively connected to the control circuit board and the electrode knife.

As a further improvement of the present invention, the flexible conveying line slat includes an outer portion located outside the smoking tube and an inner portion located inside the smoking tube, and an opening is provided at the inner end of the smoking tube inside the housing to allow the flexible conveyor line slats pass through.

As a further improvement of the present invention, a shaping mechanism is provided inside the smoking pipe near the inner end, the shaping mechanism exerts pressure on both sides of the flexible conveying line slat, so that the cross section of the flexible conveying line slat becomes arc-shaped, the cross-sectional curvature of the flexible conveyor line slat gradually decreases along the bidirectional extension direction from the part located on the shaping mechanism.

As a further improvement of the present invention, the two sides of the inner part of the tube facing and facing away from the outer part of the tube are respectively recorded as the first side and the second side, the shaping mechanism includes a middle shaping arm connected to the inner wall of the smoking pipe and two side shaping arms, the end of the middle shaping arm exerts pressure on the middle part of the first side, and the two side shaping arms exert pressure on both sides of the second side respectively.

As a further improvement of the present invention, the ends of the middle shaping arm and the side shaping arm are provided with shaping balls that can roll in any direction, and the shaping balls are aligned with the middle part of the first side or the second side, apply pressure to the sides.

As a further improvement of the present invention, there are two middle shaping arms, which are spaced apart from each other, and the two side shaping arms are located between the two middle shaping arms.

As a further improvement of the present invention, the smoking pipe is provided with an LED lampshade at the outer port outside the housing, the inner part of the pipe includes a main body section, a first branch section and a second branch section connected in parallel to the main body section, the first branch section is the branch section is connected to the electrode blade, and the second branch section is connected to the LED lampshade.

As a further improvement of the present invention, the shaping mechanism acts on the main body section, and the first branch section and the second branch section form a bifurcated structure at a parallel connection, so that the first branch section and the second branch section are spaced apart from each other.

As a further improvement of the present invention, the main body section and the first branch section extend in the same direction, and the second branch section is bent and extended from the bifurcation structure in an extension direction deviating from the first branch section, and then along the bend and extend parallel to the extending direction of the first branch segment.

As a further improvement of the present invention, a guide structure is provided in the smoking pipe for guiding the portion of the second branch section that is parallel to the first branch section.

Beneficial Effects of the Present Invention

The flexible conveying line slats have the characteristics of bending and folding, so that the flexible conveying line slats basically do not contact the inner wall of the casing and the inner wall of the smoking pipe during the extension path, thereby greatly reducing the frictional resistance during the expansion and contraction process, this allows doctors to more easily adjust the blade length according to surgical needs, which is beneficial to surgical operations.

BRIEF DESCRIPTION OF DRAWINGS

The preferred embodiments of the present invention will be described in detail below through the accompanying drawings to help understand the purpose and advantages of the present invention, wherein.

DETAILED DESCRIPTION OF THE EMBODIMENTS

The present invention will be further described in detail below based on the accompanying drawings and implementation examples.

The terms "upper, lower, left, right, front, back, front, back, top, bottom, etc." mentioned or possibly mentioned in this specification are defined relative to the structure shown in each drawing, the words "Inside" and "outside" refer to the direction toward or away from the geometric center of a specific component respectively, they are relative concepts, and therefore may change accordingly according to their different locations and different usage states. Therefore, these or other directional terms should not be construed as restrictive terms.

Figure 1:
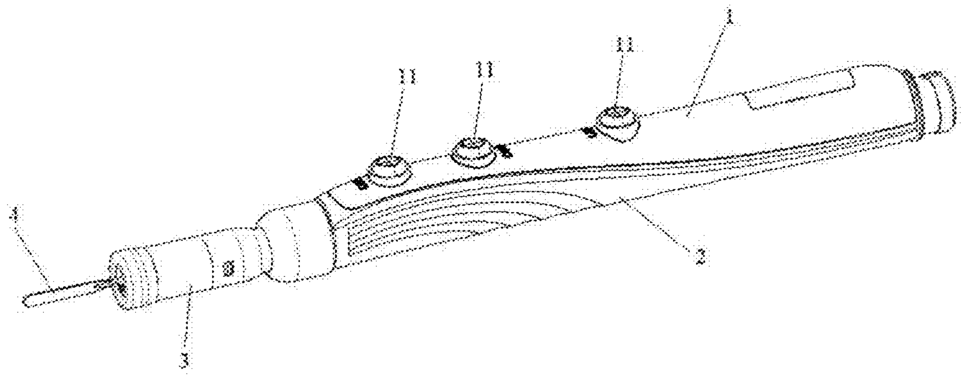
FIG. 1 is a schematic diagram of the structure of the surgical smoking knife in this implementation case.
Figure 2:
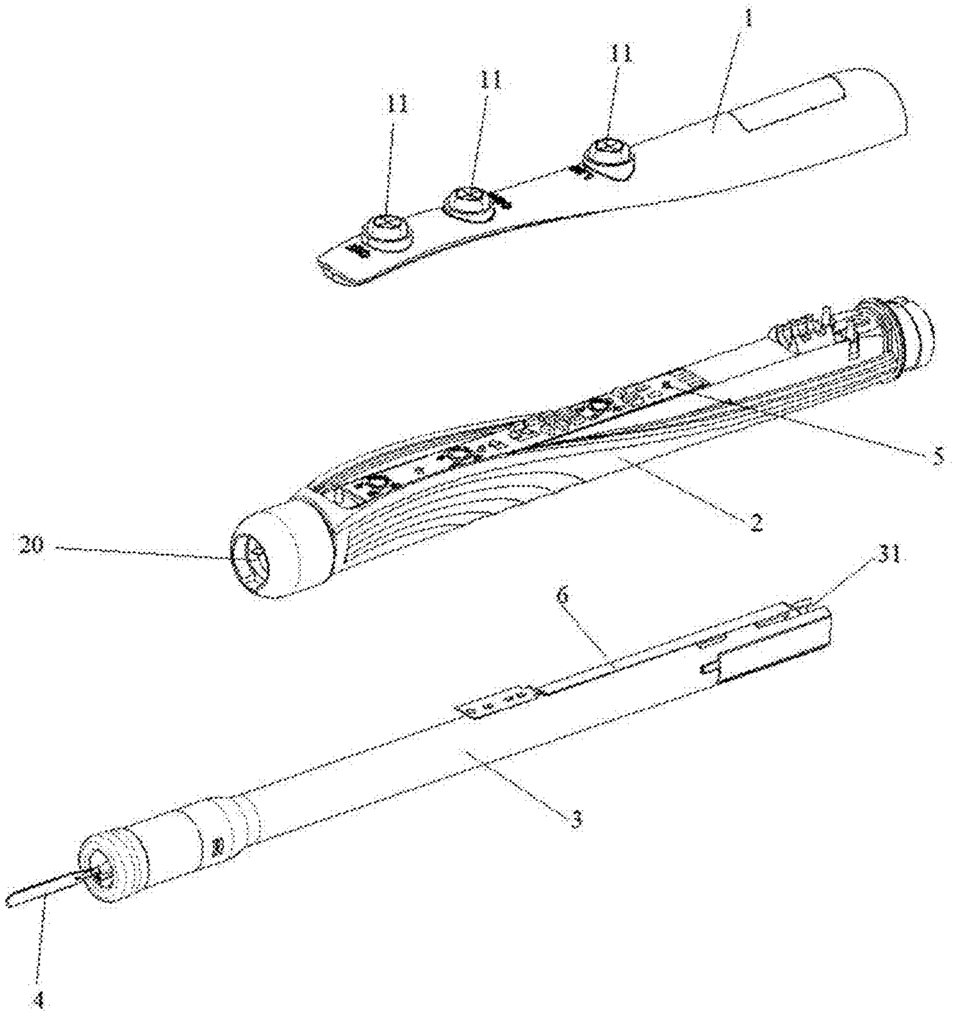
FIG. 2 is a schematic diagram of the explosion of the surgical smoking knife in this implementation case.
Figure 3:
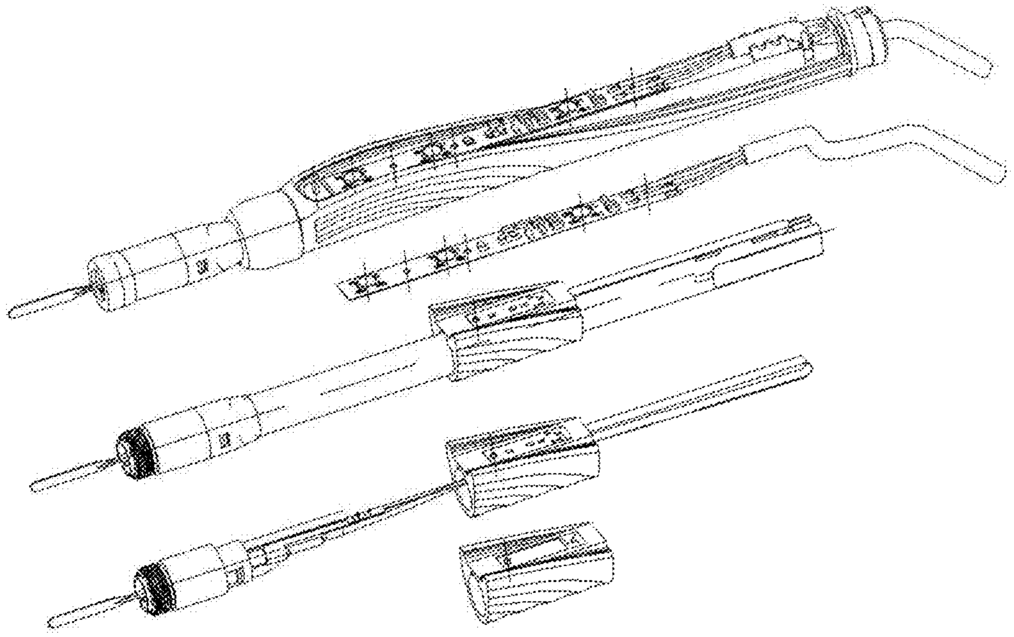
FIG. 3 is a schematic diagram of the step-by-step disassembly of the surgical smoking knife in this implementation case; (a section of the housing 3 is intercepted in the picture)
Figure 4:
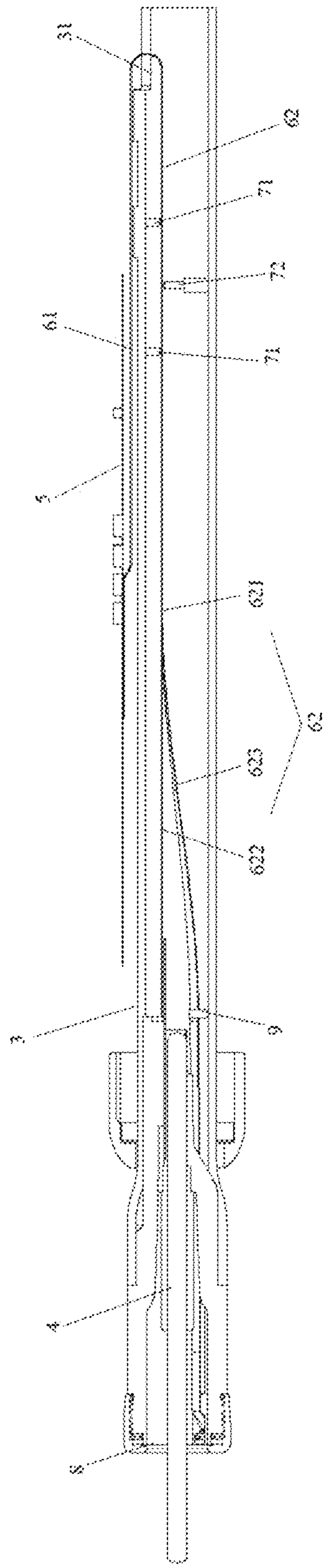
FIG. 4 is a schematic cross-sectional view of the smoking pipe in this implementation case.
Figure 5:
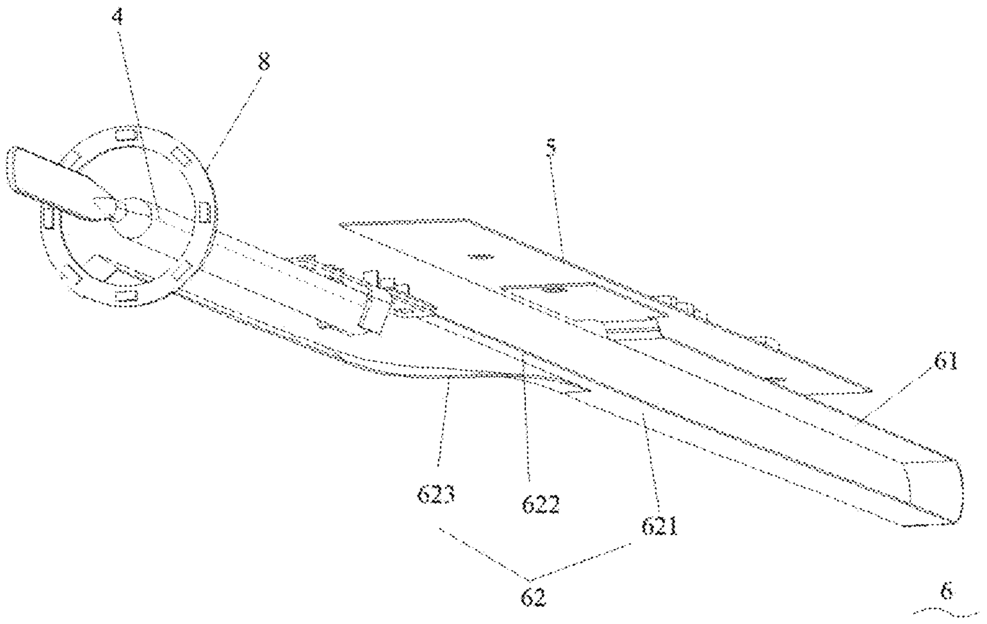
FIG. 5 is a schematic structural diagram of the control circuit board and flexible transmission circuit slats in this implementation case.
Figure 6:
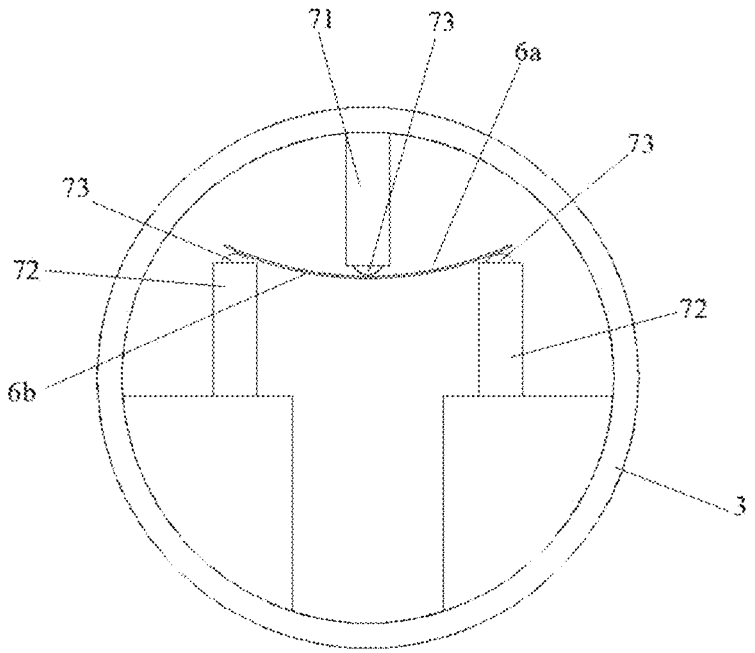
FIG. 6 is a schematic diagram of the relationship between the flexible conveying line slats, the middle shaping arm and the side shaping arm in this implementation case.
Figure 7:
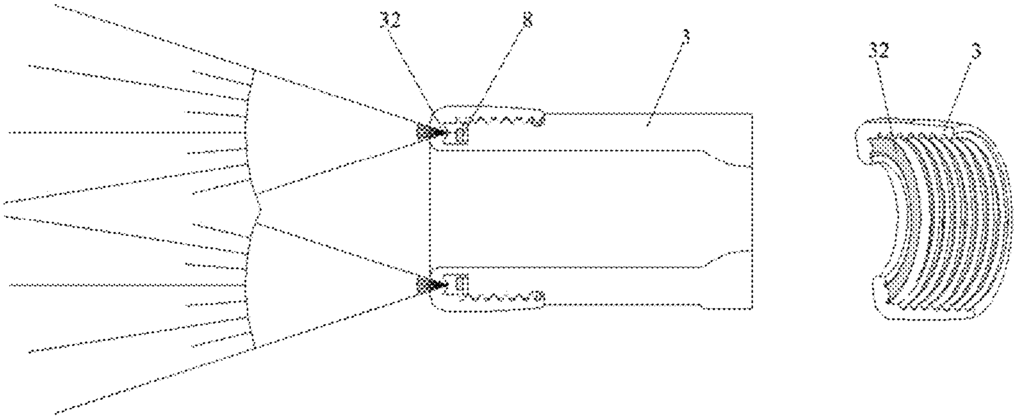
FIG. 7 is a schematic diagram of the outer end structure of the smoking pipe in this implementation case.

A surgical smoking knife, refer to FIG. 1-FIG. 7, including a housing cover 1, a housing 2, a smoking pipe 3, an electrode knife 4, a control circuit board 5, and a flexible transmission circuit slat 6. Wherein, the housing 2 is configured as a hollow structure with a linear slide 20 inside, and the slide 20 is formed with a through hole at one end of the housing 2. The smoking pipe 3 is slidably connected in the slide 20. A part of the smoking pipe 3 is located inside the housing 2, and the other part passes through the opening and is located outside the housing 2. The electrode blade 4 is assembled on the smoking pipe 3. The control circuit board 5 is arranged on the housing 2, and the slide 20 of the flexible conveying circuit slat 6 penetrates into the inside of the smoking pipe 3, and its two ends are connected to the control circuit board 5 and the electrode respectively knife 4. The housing cover 1 is connected to the housing 2 to form a complete overall housing structure. A cavity is formed between the housing 2 and the housing cover 1 to accommodate the control circuit board 5. In the housing the cover 1 is provided with a button 11 for controlling electrocution or electrocoagulation.

The surgical smoking knife in this implementation case belongs to the high-frequency electrosurgical knife, which is an electrosurgical medical device that replaces the mechanical scalpel for tissue cutting. It heats the tissue through the high-frequency and high-voltage current generated by the electrode knife 4 when it comes into contact with the human body, thereby achieving the separation and coagulation of the human tissue, thereby achieving the purpose of cutting and stopping bleeding. Electrocution is a high-density electric current that rapidly raises the cell temperature to more than 100 degrees celsius. The pressure of gasification of intracellular fluids causes the cell membrane to burst. Therefore, it can be cut accurately without mechanical force, and it will produce hemostasis while cutting. Electrocoagulation relatively slowly vaporizes the fluid inside and outside the cells, causing the cells to shrink and coagulate, sealing the blood vessel walls to stop bleeding, without the need to suture the blood vessels separately. High-frequency electrosurgery will produce smoke and dust during the above-mentioned electrocution and electrocoagulation processes. The smoke and dust belong to medical waste. Improper handling of medical waste can easily cause cross-infection between doctors and patients. The smoke and dust generated at the surgical site are collected and discharged through the smoking pipe 3.

In the surgical smoking knife of this embodiment, since the smoking tube 3 is movably connected to the slide 20, the surgical smoking knife can be telescopically adjusted, which allows the doctor to adjust the extended length according to actual needs in order to better complete the surgical operation, doctors are able to make precise cuts during surgery, reducing damage to surrounding tissue and improving surgical results.

In the prior art, the control circuit board uses a PCB circuit board or an FR circuit board, the transmission connection lines or transmission connection plates connected to these two circuit boards have poor bendability and are not in contact with the inner wall and the inner wall of the housing 2, the frictional resistance generated between the inner walls of the smoking tube 3 is relatively large, which makes it more laborious for doctors to extend and retract the smoking tube 3, which is not conducive to surgical operations.

In this implementation case, flexible transmission circuit strips 6 are used to replace the existing transmission connection lines, the flexible circuit board is also called FPC (Flexible Printed Circuit) circuit board, which is usually made of polyester or polyimide material and has bendable properties. and folding properties, its easy bending feature makes the flexible conveying line slats 6 basically not contact the inner wall of the housing 2 and the inner wall of the smoking pipe 3 during the extension path, thereby greatly reducing the frictional resistance during the expansion and contraction process, allowing doctors to more easily In order to easily adjust the blade length according to the surgical needs, it is beneficial to the surgical operation, in addition, the control circuit board 5 also uses a flexible circuit board, that is, an FPC circuit board.

In this embodiment, the flexible conveying line strip 6 includes an outer part 61 located outside the smoking pipe 3 and an inner part 62 located inside the smoking pipe 3, the smoking pipe 3 is located at the inner end of the housing 2, an opening 31 is provided, allowing the flexible conveyor line strip 6 to pass through. That is, the flexible conveying line slat 6 first winds around the inner end of the smoking pipe 3 in the channel, and then extends into the inside of the smoking pipe 3. Its routing method and overall length can match the larger expansion and contraction range of the smoking pipe 3. In addition, the port at the inner end of the smoking tube 3 can be used as the opening 31, or a notch connecting the port can be opened on the wall of the smoking tube 3, and the port and the notch can be used as the opening 31.

When the smoking tube 3 is in the maximum contraction state, the outer part 61 and the inner part 62 of the tube are basically in a straight state, as the smoking tube 3 gradually extends, the expansion of the flexible conveying line slat 6 the progress will gradually decrease, especially the outer part 61 of the tube will become looser, and when the smoking tube 3 is in the maximum extended state, the flexible conveying line slat 6, especially the outer part 61 of the tube, is in the most relaxed state, the portion 61 is substantially curved, on the one hand, the flexible conveying line slats 6 in a relaxed state are prone to "looping" phenomenon, at this time, if the smoking pipe 3 is quickly retracted and slid inward, the flexible conveying line slats 6 will be pulled, it is easy to affect the connection at both ends. Even if the flexible conveying line slats 6 do not loop, when the smoking pipe 3 shrinks rapidly, the expansion and recovery speed of the flexible conveying line slats 6 cannot match the sliding speed of the smoking pipe 3, which will cause the smoking pipe 3 to collapse, the inner end of the smoking tube 3 will directly hit the outer part 61 of the tube and cause damage. It is also possible that the inner end of the smoking tube 3 is stuck on the outer part 61 of the tube, so that the outer part 61 of the tube is connected to the control circuit board 5 from one end to the other end, it may happen that the stuck section is over-tightened, stretched or even broken.

In order to solve this technical problem in this implementation case, the smoking pipe 3 is provided with a shaping mechanism near the inner end. The shaping mechanism exerts pressure on both sides of the flexible conveying line slat 6 so that the cross-section of the flexible conveying line slat 6 is in the shape of curved, the curvature of the end surface of the flexible conveyor line slat 6 gradually decreases along the bidirectional extension direction from the part located on the shaping mechanism until its cross-section becomes straight. Since the rigidity of the flexible conveying line slat 6 is proportional to the curvature of its cross-section, a section of the flexible conveying line slat 6 extending in both directions with the part located at the shaping mechanism as the midpoint has sufficient rigidity to enable the flexible conveying line slat 6 to 6 keep it straight. First of all, when the smoking pipe 3 is in the maximum extended state, only the part of the outer part 61 of the pipe close to the connection control circuit board 5 is in a relaxed and bent state, which can effectively avoid the "looping" phenomenon of the flexible conveying circuit slat 6, thereby when the sliding smoking pipe 3 is quickly retracted, the pulling effect on the flexible conveying line slat 6 can be avoided; secondly, the outer part 61 of the flexible conveying line slat 6 remains straight near the inner end of the smoking pipe 3 state, so that when the smoking pipe 3 retracts and slides quickly, the inner end of the smoking pipe 3 can directly hit the outer part 61 of the pipe or get stuck on the outer part 61 of the pipe, thereby preventing the outer part 61 of the pipe from being directly hit or stuck. It happens that it is pulled off due to the failure. Furthermore, the shaping mechanism only strengthens the rigidity of a part of the flexible conveying line slat 6 and will not affect the normal bending change of the flexible conveying line slat 6 when the smoking pipe 3 telescopically slides.

In this embodiment, the two sides of the inner part 62 of the tube facing and facing away from the outer part 61 of the tube are respectively marked as the first side 6*a* and the second side 6*b*, the shaping mechanism includes a middle shaping arm connected to the inner wall of the smoking pipe 3 71 and two side shaping arms 72, the end of the middle shaping arm 71 exerts pressure on the middle part of the first side 6*a*, and the two side shaping arms 72 exert pressure on both sides of the second side 6*b* respectively. During the telescopic sliding process of the smoking tube 3, due to changes in the bending shape and degree of the outer part 61 of the tube, the push-pull force exerted on the inner part 62 of the tube changes. Therefore, during this process, the inner part 62 of the tube will move relative to the shaping mechanism, a certain displacement occurs along the length direction of the smoking tube 3, so it is necessary to minimize the frictional resistance of the shaping mechanism to the inner part 62 of the tube, in this embodiment, the central shaping arm 71 and the two side shaping arms 72 are used to applying pressure to the middle of first side 6*a* and both sides of the second side 6*b* can minimize the contact area between the shaping mechanism and the inner part 62 of the tube, thereby minimizing the friction between the two forces are minimized.

During the telescopic sliding process of the smoking pipe 3, the flexible conveying line slats 6 will also deflect along the width direction of the smoking pipe 3, that is, the inner part 62 of the pipe and the shaping mechanism will be opposite to each other along the length and width directions of the smoking pipe 3, displacement will not only generate friction resistance, but also easily cause wear on both sides of the flexible conveyor line slat 6, namely the first side 6*a* and the second side 6*b*, based on this, in this implementation case, the ends of the middle shaping arm 71 and the side shaping arms 72 are provided with shaping balls 73 that can roll in any direction, the shaping balls 73 are aligned with the middle of the first side 6*a* or the side of the second side 6*b*. put pressure on. therefore, when the inner part 62 and the shaping mechanism are relatively displaced along the length and width directions of the smoking pipe 3, the shaping balls 73 will roll in the corresponding directions, so that the frictional resistance generated in the two directions is relatively slight, not only it is beneficial to the telescopic sliding of the smoking pipe 3 and will not cause wear to the first side 6*a* and the second side 6*b* of the flexible conveying line slat 6.

More specifically, the middle shaping arm 71 and the side shaping arm 72 are provided with a cavity for accommodating the shaping balls 73, and a circular opening connected to the cavity is opened at the end, the diameter of the opening is smaller than the diameter of the shaping ball, so that a part of the shaping ball 73 is exposed and contacts the first side 6*a* or the second side 6*b*.

In this embodiment, there are two middle shaping arms 71, which are spaced apart from each other, the two side shaping arms 72 are located between the two middle shaping arms 71, that is, the shaping mechanism and the flexible conveyor. there are only four contact points on the first side 6*a* and the second side 6*b* of the circuit slat 6, which not only minimizes frictional resistance, but also extends the length of the rigid section of the flexible conveyor circuit slat 6.

In this embodiment, the smoking pipe 3 is provided with an LED lampshade 8 at the outer port outside the housing 2, the LED lampshade 8 includes a ring body and a plurality of LED light sheets arranged around the ring body, the inner part 62 of the tube includes a main body section 621, a first branch section 622 and a second branch section 623 connected in parallel to the main body section 621, the first branch section 622 is connected to the electrode blade 4, and the second branch section 623 is connected to the LED lampshade 8 connections. The surgical smoking knife in this embodiment not only has the functions of electric cutting and electrocoagulation, but also has the function of lighting, the LED lampshade 8 can telescopically slide along with the smoking tube 3 to illuminate the surgical site, which is beneficial to the doctor's surgical operation.

In this embodiment, the shaping mechanism acts on the main body section 621, and the first branch section 622 and the second branch section 623 form a bifurcated structure at the parallel connection, so that the first branch section 622 and the second branch section segments 623 are spaced apart from each other, in addition to strengthening the rigidity and allowing the flexible conveying line slats 6 to undergo relative displacement along the length and width directions of the smoking pipe 3, the shaping mechanism can also connect the inner part 62 of the pipe to the click knife and the LED due to frictional force, the portion between the lampshade 8 and the shaping mechanism is tightened to prevent the first branch section 622 and the second branch section 623 from being entangled with each other.

In this embodiment, the main body section 621 and the first branch section 622 extend in the same direction, and the second branch section 623 is bent and extended from the bifurcation structure in an extension direction deviating from the first branch section 622, then bending and extending along the direction parallel to the extension of the first branch section 622, the first branch section 622 and the second branch section 623 are spaced apart from each other, which can further reduce the situation that the first branch section 622 and the second branch section 623 are entangled with each other. occur.

In this embodiment, the smoking pipe 3 is provided with a guide structure 9 for guiding the part of the second branch section 623 parallel to the first branch section 622, so that the first branch section 622 and the second branch section a gap is stably generated between the segments 623, and the guide structure 9 can be configured as a buckle connected to the inner wall of the smoking pipe 3, and the buckle is buckled on the second branch segment 623.

In this embodiment, the smoking pipe 3 is provided with a light condensing refraction ring 32 on the annular edge of its outer end, the inner surface of the light concentrating refraction ring 32 is a convex surface, the light emitted by the LED lampshade 8 passes through the light condensing refraction ring 32, it has the function of concentrating light, improves the lighting effect, and is beneficial to surgical operations.

Finally, it should be noted that the above implementation examples are only used to illustrate the technical solution of the present invention, but not to limit it; although the present invention has been described in detail with reference to the foregoing implementation examples, those of ordinary skill in the art should understand that it can still be used modifications are made to the technical solutions recorded in the foregoing embodiments, or equivalent substitutions are made to some of the technical features; however, these modifications or substitutions do not cause the essence of the corresponding technical solutions to depart from the scope of the technical solutions in each embodiment of the present invention.

What is claimed is:

1. A surgical smoking knife, comprising:

a housing with a slideway inside;

a smoking pipe is slidably connected to the slideway, with one part located inside the housing and the other part located outside the housing;

an electrode knife is arranged on the smoking pipe;

a control circuit board is provided on the housing;

a flexible conveying circuit slat penetrates into an interior of the smoking pipe through the slideway, and its two ends are respectively connected to the control circuit board and the electrode knife;

the flexible conveying circuit slat includes an outer portion located outside the smoking pipe and an inner portion located inside the smoking pipe; an opening is provided at an inner end of the smoking pipe to allow the flexible conveying circuit slat to pass through; the smoking pipe is provided with a shaping mechanism near the inner end of the smoking pipe; the shaping mechanism exerts pressure on both sides of the flexible conveying circuit slat to form an arcuate cross-section of the flexible conveying circuit slat; a curvature of the arcuate cross-section gradually decreases along a bidirectional extension direction from a part located at the shaping mechanism; two surfaces that face the inner portion of the smoking pipe and face away from the outer portion of the smoking pipe are respectively marked as a first surface and a second surface; the shaping mechanism includes a middle shaping arm and two side shaping arms on an inner wall of the smoking pipe; an end of the middle shaping arm exerts pressure on a middle part of the first surface, and ends of the two side shaping arms respectively exert pressure on both side parts of the second surface.

2. The surgical smoking knife of claim 1, wherein the ends of the middle shaping arm and the ends of the two side shaping arms are provided with shaping balls that can roll in any direction, and the shaping balls exert pressure on the middle part of the first surface or the side part of the second surface.

3. The surgical smoking knife of claim 1, wherein there are two middle shaping arms, which are spaced apart from each other, and the two side shaping arms are located between the two middle shaping arms.

4. The surgical smoking knife of claim 1, wherein the smoking pipe is provided with an LED lampshade at an outer port outside the housing; the inner portion of the smoking pipe includes a main body section, a first branch section and a second branch section connected in parallel to the main body section, the first branch section is connected to the electrode knife and the second branch section is connected to the LED lampshade.

5. The surgical smoking knife of claim 4, wherein the shaping mechanism acts on the main body section, and the first branch section and the second branch section form a bifurcated structure at a parallel connection, so that the first branch section and the second branch section are spaced apart from each other.

6. The surgical smoking knife of claim 5, wherein the main body section and the first branch section extend in the same direction; the second branch section bends and extends from the bifurcated structure in a direction deviating from an extending direction of the first branch section, and then bends and extends along a direction parallel to the extending direction of the first branch section.

7. The surgical smoking knife of claim 6, wherein a guide structure is provided in the smoking pipe for guiding the portion of the second branch section that is parallel to the first branch section.

* * * * *